(12) United States Patent
Cosenza et al.

(10) Patent No.: US 9,458,240 B2
(45) Date of Patent: Oct. 4, 2016

(54) ANTI-BAFFR ANTIBODY FORMULATIONS

(75) Inventors: Marta Cosenza, Basel (CH);
Christoph Heusser, Oberwil (CH);
Julia Neugebauer, Munich (DE);
Eveline Schaadt, Munich (DE);
Stefanie Urlinger, Munich (DE);
Maximilian Woisetschlaeger, Oberwill (CH)

(73) Assignee: Novartis Pharma AG, Basel (CH)

( * ) Notice: Subject to any disclaimer, the term of this patent is extended or adjusted under 35 U.S.C. 154(b) by 359 days.

(21) Appl. No.: 13/991,984

(22) PCT Filed: Dec. 8, 2011

(86) PCT No.: PCT/EP2011/072248
§ 371 (c)(1),
(2), (4) Date: Jan. 15, 2014

(87) PCT Pub. No.: WO2012/076670
PCT Pub. Date: Jun. 14, 2012

(65) Prior Publication Data
US 2014/0186373 A1 Jul. 3, 2014

Related U.S. Application Data

(60) Provisional application No. 61/421,650, filed on Dec. 10, 2010.

(51) Int. Cl.
| | | |
|---|---|---|
| A61K 39/395 | (2006.01) |
| C07K 16/18 | (2006.01) |
| C07K 16/28 | (2006.01) |
| A61K 9/00 | (2006.01) |
| A61K 9/08 | (2006.01) |
| A61K 9/19 | (2006.01) |
| A61K 47/18 | (2006.01) |
| A61K 47/26 | (2006.01) |
| C07K 14/715 | (2006.01) |
| A61K 39/00 | (2006.01) |

(52) U.S. Cl.
CPC ......... *C07K 16/2878* (2013.01); *A61K 9/0019* (2013.01); *A61K 9/08* (2013.01); *A61K 9/19* (2013.01); *A61K 39/39591* (2013.01); *A61K 47/183* (2013.01); *A61K 47/26* (2013.01); *A61K 39/3955* (2013.01); *A61K 39/39533* (2013.01); *A61K 2039/505* (2013.01); *C07K 2317/21* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 2008/0181888 A1* | 7/2008 | Ambrose | ........... | C07K 16/2878 424/133.1 |
| 2010/0021452 A1* | 1/2010 | Heusser | ............ | C07K 16/2878 424/130.1 |

FOREIGN PATENT DOCUMENTS

| | | |
|---|---|---|
| WO | 2004/055164 A2 | 7/2004 |
| WO | 2006/044908 A2 | 4/2006 |
| WO | 2006/073941 A2 | 7/2006 |
| WO | 2008/008482 A2 | 1/2008 |
| WO | 2010/007082 A1 | 1/2010 |
| WO | 2010/069858 A1 | 6/2010 |
| WO | 2010/100200 A2 | 9/2010 |

OTHER PUBLICATIONS

Kerwin, B.A. Polysorbates 20 and 80 used in the formulation of protein biotherapeutics: structure and degradation pathways. J Pharmaceut Sci 97(8): 2924-2935, 2008.*
Lee et al., "Synthetic anti-BR3 Antibodies that mimic BAFF binding and target both human and murine B cells," Blood 108(9):3103-3111 (2006).
Lin et al., "AntiOBR3 antibodies: a new class of B-cell immunotherapy combining cellular depletion and survival blockade," Blood 110(12): 3959-3967 (2007).
Eisenberg, Robert, "Combination biologics: 1 stone, 2 birds," Blood 110(12):3817 (Dec. 2007).
Ng et al., "B Cell-Activating Factor Belonging to the TNF Family (BAFF)-R Is the Principal BAFF Receptor Facilitation BAFF Constimulation of Circulating T and B Cells," J Immunology 173(2):807-817 (2004).
Zhang et al., "BAFF supports human B cell differentiation in the lymphoid follicles through distinct receptors," International Immunology 17(6):779-788 (2005).
Breen et al., "Effect of Moisture on the Stability of a Lyophilized Humanized Monoclonal Antibody Formulation," Pharmaceutical Research 18(9):1345-1353 (Sep. 2001).
He et al., "High Throughput Thermostability Screening of Monoclonal Antibody Formulations," Journal of pharmaceutical Sciences 99(4):1707-1720 (Apr. 2010).
Daugherty et al., "Formulation and delivery issues for monoclonal antibody therapeutics," Advanced Drug Delivery Reviews 58(5-6):686-706 (2006).
Manning et al., "Stability of Protein Pharmaceuticals: An Update," Pharmaceutical Research 27(4):544-575 (Apr. 2010).
Garidel et al., "A thermodynamic analysis of the binding interaction between polysorbate 20 and 80 with human serum albumins and immunoglobulins: A contribution to understand colloidal protein stabilisation," Biophysical Chemistry 143 (1-2):70-78 (2009).

* cited by examiner

*Primary Examiner* — Bridget E Bunner
(74) *Attorney, Agent, or Firm* — Grace S. Law

(57) ABSTRACT

Anti-BAFFR antibodies are formulated as lyophilisate or liquid formulation. The lyophilisates can be reconstituted to give a solution with a high concentration of the antibody active ingredient for delivery to a patient without high levels of antibody aggregation. The lyophilisate can be reconstituted with an aqueous reconstituent to provide an aqueous composition in which the antibody has a concentration of at least 50 mg/ml. The lyophilisate or aqueous pharmaceutical composition may include one or more of a sugar, a buffering agent, a surfactant, and/or a free amino acid.

16 Claims, No Drawings

ANTI-BAFFR ANTIBODY FORMULATIONS

SEQUENCE LISTING

The instant application contains a Sequence Listing which has been submitted in ASCII format via EFS-Web and is hereby incorporated by reference in its entirety. Said ASCII copy, created on Jul. 18, 2013, is named PAT 053990-US-PCT_ST 25.txt and is 14,928 bytes in size.

TECHNICAL FIELD

The present invention relates to a pharmaceutical formulation of an antibody against BAFFR (BAFF receptor), a process for the preparation thereof and uses of the formulation.

BACKGROUND

The BAFFR:BAFF pair is critically involved in the maturation of transitional B-cells, for survival and activation of mature B-cells, and for isotype class switching in response to T cell-dependent antigens. BAFF and its receptor BAFFR are also important for survival and growth of malignant B-cells. Further, BAFFR normally is not expressed on pre-B cells, but was recently shown to be expressed on human ALL (B-lineage acute lymphoblastic leukemia) cells (Parameswaran, 2010, Cancer Res. 70(11) 4346-4356). The removal of autoreactive B cells and the blockade of inappropriate survival/activation mediated by excess BAFF levels in patients suffering from autoimmune disorders or cancer represents a well-validated therapeutic goal. Thus, an anti-BAFFR antibody, in particular an antibody capable of antibody-dependent cell-mediated cytotoxicity (ADCC) and blockade of ligand binding to BAFFR may offer an effective therapeutic agent in autoimmune diseases and B cell neoplasms.

Antibodies against BAFFR are known from e.g. WO 2010/007082 and include antibodies which are characterized by comprising a $V_H$ domain with the amino acid sequence of SEQ ID NO: 1 and a $V_L$ domain with the amino acid sequence of SEQ ID NO: 2. The antibody MOR6654 is one such antibody (IgG1 kappa). It has the heavy chain amino acid sequence of SEQ ID NO: 9 and the light chain amino acid sequence of SEQ ID NO: 10. This antibody may be expressed from SEQ ID NOs: 14 and 15, preferably in a host cell which lacks fucosyl-transferase, for example in a mammalian cell line with an inactive FUT8(−/−) gene, to give a functional non-fucosylated anti-BAFFR antibody with enhanced ADCC. This antibody is referred to hereafter as MOR6654B. Alternative ways to produce non-fucosylated antibodies are known in the art.

Formulations with high concentration of antibody may have short shelf lives and the formulated antibodies may loose biological activity resulting from chemical and physical instabilities during the storage. Among those, aggregation, deamidation and oxidation are known to be the most common causes of antibody degradation. In particular, aggregation can potentially lead to increased immune response in patients, leading to safety concerns. Thus it must be minimized or prevented.

It is an object of the invention to provide further and improved formulations of anti-BAFFR antibodies, and in particular formulations with high concentration of anti-BAFFR antibodies and low levels of antibody aggregation.

DISCLOSURE OF THE INVENTION

Therapeutic antibodies are typically formulated either in aqueous form ready for parenteral administration or as lyophilisates for reconstitution with a suitable diluent prior to administration. According to the invention, an anti-BAFFR antibody may be formulated either as a lyophilisate, or as an aqueous composition, for example in pre-filled syringes. Suitable formulation can provide an aqueous pharmaceutical composition or a lyophilisate which can be reconstituted to give a solution with a high concentration of the antibody active ingredient and a low level of antibody aggregation for delivery to a patient. High concentrations of antibody are useful as they reduce the amount of material which must be delivered to a patient. Reduced dosing volumes minimize the time taken to deliver a fixed dose to the patient. The aqueous compositions of the invention with high concentration of anti-BAFFR antibodies are particularly suitable for subcutaneous administration.

Thus the invention provides an aqueous pharmaceutical composition, suitable for parenteral administration in a subject, e.g., for subcutaneous administration, comprising an anti-BAFFR antibody.

The following specific embodiments of the invention are described as numbered hereafter:

1. An aqueous pharmaceutical composition, suitable for subcutaneous administration in a subject, comprising an anti-BAFFR antibody in which the antibody has a concentration of at least 50 mg/ml, and wherein said anti-BAFFR antibody includes: (i) one or more heavy chain CDRs selected from the group consisting of SEQ ID NOs: 3, 4 and 5; and/or (ii) one or more light chain CDRs selected from the group consisting of SEQ ID NOs: 6, 7 and 8.
2. The aqueous pharmaceutical composition, suitable for subcutaneous administration in a subject, according to Embodiment 1, wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8.
3. The aqueous pharmaceutical composition of Embodiment 1 or 2, wherein the anti-BAFFR antibody comprises a $V_H$ domain with amino acid SEQ ID NO: 1 and a $V_L$ domain with amino acid SEQ ID NO: 2.
4. The aqueous pharmaceutical composition of Embodiment 1, 2 or 3, wherein the anti-BAFFR antibody comprises a heavy chain region of SEQ ID NO: 9 and a light chain region of SEQ ID NO: 10.
5. The aqueous pharmaceutical composition of any one of Embodiments 1 to 4, wherein less than 5% of the anti-BAFFR antibody is aggregated or degraded.
6. The aqueous pharmaceutical composition of any one of Embodiments 1 to 5, comprising one or more of the following components selected among the group consisting of: a stabilizer, a buffering agent; and a surfactant.
7. The aqueous pharmaceutical composition of Embodiment 6, wherein the stabilizer is a sugar.
8. The aqueous pharmaceutical composition of Embodiment 6 or 7, comprising: a sugar, a buffering agent, and a surfactant.
9. The aqueous pharmaceutical composition of Embodiment 6 or 7, further comprising a free amino acid.
10. The aqueous pharmaceutical composition of Embodiment 7 to 9, comprising sucrose as a sugar.
11. The aqueous pharmaceutical composition of Embodiment 10, comprising 200-300 mM sucrose.
12. The aqueous pharmaceutical composition of Embodiments 6-11, comprising a histidine buffer as the buffering agent.
13. The aqueous pharmaceutical composition of Embodiment 12, comprising 25-35 mM histidine buffer.

14. The aqueous pharmaceutical composition of Embodiments 6 to 13, comprising polysorbate 80 as a surfactant.
15. The aqueous pharmaceutical composition of Embodiment 14, comprising 0.01 to 0.1% polysorbate 80.
16. The aqueous pharmaceutical composition of Embodiment 9, further comprising arginine as free amino acid.
17. The aqueous pharmaceutical composition of Embodiment 16, comprising 40-80 mM arginine.
18. The aqueous pharmaceutical composition of any preceding Embodiment, comprising sucrose, a histidine buffer, polysorbate 80 and arginine.
19. A lyophilisate suitable for preparing the aqueous pharmaceutical composition of any preceding Embodiments.
20. A lyophilisate according to Embodiment 19, comprising sucrose, a histidine buffer, polysorbate 80 and arginine.
21. A method for preparing a lyophilisate, comprising the steps of: (i) preparing an aqueous solution comprising an anti-BAFFR antibody, a sugar, a buffering agent, a surfactant and optionally a free amino acid; and (ii) lyophilizing the aqueous solution.
22. A delivery device including the aqueous pharmaceutical composition of any one of Embodiments 1-18.
23. A pre-filled syringe including the aqueous pharmaceutical composition of any one of Embodiments 1-18.
24. A method for delivering an anti-BAFFR monoclonal antibody to a mammal, comprising a step of administering to the patient a pharmaceutical composition of any one of Embodiments 1-18.
25. The composition of any one of Embodiments 1-18, for use in treating a disease or disorder that is mediated by BAFF receptor or that can be treated by killing or depleting B cells.
26. The composition of Embodiment 25, for the treatment of autoimmune diseases.
27. The composition of Embodiment 25, for the treatment of B cell neoplasms, such as lymphoma, leukemia or myeloma.
28. The composition of Embodiment 26, for the treatment of rheumatoid arthritis, systemic lupus erythematosus, or Pemphigus vulgaris.
29. The aqueous pharmaceutical composition of any one of Embodiments 1-18 in which the antibody has a concentration of at least at least 50 mg/ml, at least 100 mg/ml, at least 150 mg/ml, at least 200 mg/ml, at least 250 mg/ml, or at least 300 mg/ml.

The invention also provides an aqueous pharmaceutical composition comprising: an anti-BAFFR monoclonal antibody as described above, for example MOR6654, especially MOR6654B; a stabilizer; a buffering agent; and a surfactant. The composition preferably also includes a free amino acid.

The invention also provides a lyophilisate comprising: an anti-BAFFR monoclonal antibody as described above, for example MOR6654, especially, MOR6654B; a sugar; a buffering agent; and a surfactant. The lyophilisate preferably also includes a free amino acid.

The invention also provides a lyophilisate comprising an anti-BAFFR monoclonal antibody as described above, for example MOR6654, especially, MOR6654B, wherein the lyophilisate can be reconstituted with an aqueous reconstituent to provide an aqueous composition in which the antibody has a concentration of at least 50 mg/ml, 100 mg/ml, 150 mg/ml, 200 mg/ml, 250 mg/ml, or 300 mg/ml, after reconstitution in an aqueous solution.

The invention also provides an aqueous pharmaceutical composition comprising high concentration of an anti-BAFFR monoclonal antibody as described above, for example MOR6654, especially, MOR6654B, wherein less than 5%, 4%, 3%, 2% or 1% of the anti-BAFFR antibody is aggregated or degraded.

The invention also provides a process for preparing a lyophilisate, comprising steps of: (I) preparing an aqueous solution comprising an anti-BAFFR monoclonal antibody, a sugar, a buffering agent, a surfactant, and optionally a free amino acid; and (ii) lyophilizing the aqueous solution.

The invention also provides a process for preparing a pharmaceutical composition, comprising a step of mixing a lyophilisate with an aqueous reconstituent, wherein the lyophilisate comprises an anti-BAFFR monoclonal antibody, a sugar, a buffering agent, a surfactant, and optionally a free amino acid.

More specifically the invention provides a lyophilized formulation prepared by lyophilizing an aqueous formulation having a pH of 5.0-7.0 and comprising
  (i) an anti-BAFFR antibody wherein the antibody has a concentration of 20-120 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
  (ii) a stabilizer,
  (iii) a buffering agent,
  (iv) a surfactant, and optionally
  (v) an amino acid.

In one embodiment said lyophilized formulation is prepared from an aqueous formulation having a pH of 5.0-7.0 and comprising
  (i) an anti-BAFFR antibody wherein the antibody has a concentration of 20-120 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
  (ii) sucrose or trehalose as a stabilizer,
  (iii) histidine as a buffering agent,
  (iv) polysorbate 80 as a surfactant, and optionally
  (v) an amino acid selected from arginine and glycine.

In one embodiment said lyophilized formulation is prepared from an aqueous formulation having a pH of 5.0-7.0 and comprising
  (i) an anti-BAFFR antibody wherein the antibody has a concentration of 20-120 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
  (ii) 3-300 mM sucrose or trehalose as a stabilizer,
  (iii) 1-60 mM histidine as a buffering agent,
  (iv) up to 0.2% polysorbate 80 as a surfactant, and optionally
  (v) 2-80 mM arginine or glycine.

In one embodiment said lyophilized formulation is prepared from an aqueous formulation having a pH of 6.5 and comprising
  (i) an anti-BAFFR antibody wherein the antibody has a concentration of 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
  (ii) 90 mM sucrose as a stabilizer,
  (iii) 7 mM histidine as a buffering agent, and
  (iv) 0.02% polysorbate 80 as a surfactant.

In one embodiment said lyophilized formulation is prepared from an aqueous formulation having a pH of 6.5 and comprising
(i) an anti-BAFFR antibody wherein the antibody has a concentration of 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 90 mM sucrose as a stabilizer,
(iii) 7 mM histidine as a buffering agent,
(iv) 0.02% polysorbate 80 as a surfactant, and
(v) 20 mM glycine-HCl.

In one embodiment said lyophilized formulation is prepared from an aqueous formulation having a pH of 6.5 and comprising
(i) an anti-BAFFR antibody wherein the antibody has a concentration of 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 90 mM sucrose as a stabilizer,
(iii) 7 mM histidine as a buffering agent,
(iv) 0.02% polysorbate 80 as a surfactant, and
(v) 17 mM arginine-HCl.

In one embodiment said lyophilized formulation is prepared from an aqueous formulation having a pH of 6.5 and comprising
(i) an anti-BAFFR antibody wherein the antibody has a concentration of 66.6 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 90 mM sucrose as a stabilizer,
(iii) 7 mM histidine as a buffering agent,
(iv) 0.02% polysorbate 80 as a surfactant, and
(v) 17 mM arginine-HCl.

The invention also provides an aqueous pharmaceutical composition obtained by reconstituting a lyophilized formulation as described above, wherein the reconstitution factor is between 1:0.5 to 1:6. A reconstitution factor of 1:3 is useful.

The invention also provides an aqueous pharmaceutical composition having a pH of 5.0 to 7.0 comprising
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) a stabilizer,
(iii) a buffering agent,
(iv) a surfactant, and optionally
(v) an amino acid.

In one embodiment the aqueous pharmaceutical composition having a pH of 5.0 to 7.0 comprises
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) sucrose or trehalose as a stabilizer,
(iii) histidine as a buffering agent,
(iv) polysorbate 80 as a surfactant, and optionally
(v) an amino acid selected from arginine and glycine.

In one embodiment the aqueous pharmaceutical composition having a pH of 5.0 to 7.0 comprises
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 200-300 mM sucrose as a stabilizer,
(iii) 25-35 mM histidine as a buffering agent,
(iv) up to 0.2% polysorbate 80 as a surfactant, and optionally
(v) 10-80 mM arginine or glycine.

In one embodiment the aqueous pharmaceutical composition has a pH of 6.5 and comprises
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabilizer,
(iii) 21 mM histidine as a buffering agent, and
(iv) 0.06% polysorbate 80 as a surfactant.

In one embodiment the aqueous pharmaceutical composition has a pH of 6.5 and comprises
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabilizer,
(iii) 21 mM histidine as a buffering agent,
(iv) 0.06% polysorbate 80 as a surfactant, and
(v) 60 mM glycine.

In one embodiment the aqueous pharmaceutical composition has a pH of 6.5 and comprises
(i) an anti-BAFFR antibody wherein the antibody has a concentration of at least 50 mg/ml, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 270 mM sucrose as a stabilizer,
(iii) 21 mM histidine as a buffering agent,
(iv) 0.06% polysorbate 80 as a surfactant, and
(v) 51 mM arginine.

In one embodiment the aqueous pharmaceutical composition of the invention has a BAFFR antibody concentration of 150 mg/ml.

In one embodiment the lyophilized formulation or the aqueous pharmaceutical composition of the invention comprises an anti-BAFFR antibody comprising a $V_H$ domain with amino acid SEQ ID NO: 1 and a $V_L$ domain with amino acid SEQ ID NO: 2.

In one embodiment the lyophilized formulation or the aqueous pharmaceutical composition of the invention comprises an anti-BAFFR antibody comprising a heavy chain region of SEQ ID NO: 9 and a light chain region of SEQ ID NO: 10.

In one embodiment the lyophilized formulation or the aqueous pharmaceutical composition of the invention comprises the anti-BAFFR antibody MOR6654 or MOR6654B.

The invention also comprises a delivery device including the aqueous pharmaceutical composition of the invention.

The invention also comprises a pre-filled syringe including the aqueous pharmaceutical composition of the invention.

The invention also comprises a method for delivering an anti-BAFFR antibody to a mammal, comprising a step of administering to the patient an aqueous pharmaceutical composition of the invention.

The invention also comprises a lyophilized formulation or an aqueous pharmaceutical composition according to the invention for use in treating a disease or disorder that is mediated by BAFF receptor or that can be treated by killing or depleting B cells.

The invention also comprises a lyophilized formulation or aqueous pharmaceutical composition according to the invention for use in the treatment of autoimmune diseases.

The invention also comprises a lyophilized formulation or aqueous pharmaceutical composition according to the invention for use in the treatment of B cell neoplasms, such as lymphoma, leukemia or myeloma.

The invention also provides a lyophilized formulation or aqueous pharmaceutical composition according to the invention for use in the treatment of rheumatoid arthritis, systemic lupus erythematosus, or Pemphigus vulgaris.

Aqueous Pharmaceutical Compositions with High Concentration of Anti-BAFFR Antibodies The invention relies, at least partly, in the formulation properties of antibodies such as MOR6654 and MOR6654B, which retain remarkable stability and bioactive properties when formulated in a high concentration either as a liquid (aqueous) or lyophilisate composition.

As used herein, an "aqueous" pharmaceutical composition is a composition suitable for pharmaceutical use, wherein the aqueous carrier is distilled water. A composition suitable for pharmaceutical use may be sterile, homogeneous and/or isotonic. Aqueous pharmaceutical compositions may be prepared either directly in an aqueous form, for example in pre-filled syringe ready for use (the "liquid formulations") or as lyophilisate to be reconstituted shortly before use. As used herein, the term "aqueous pharmaceutical composition" refers to the liquid formulation or reconstituted lyophilized formulation. In certain embodiments, the aqueous pharmaceutical compositions of the invention are suitable for parenteral administration to a human subject. In a specific embodiment, the aqueous pharmaceutical compositions of the invention are suitable for subcutaneous administration.

As used herein, the phrase "parenteral administration" means mode of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of therapeutic antibodies to a pharmaceutical grade are well known in the art.

The composition will usually be non-pyrogenic e.g. containing <1 EU (endotoxin unit, a standard measure) per dose, and preferably <0.1 EU per dose. The composition is preferably gluten-free.

In specific embodiments, the aqueous pharmaceutical compositions of the invention exhibit low to undetectable levels of antibody aggregation or degradation, with very little to no loss of the biological activities during manufacture, preparation, transportation and long periods of storage, the concentration of the anti-BAFFR antibody being at least about 50 mg/ml, 100 mg/ml, 150 mg/ml, 200 mg/ml, 250 mg/ml, or 300 mg/ml.

In one aspect, the invention relates to an aqueous pharmaceutical composition with high concentration of anti-BAFFR antibodies.

It is known in the art that such high concentration aqueous pharmaceutical compositions can be diluted prior to injection, for example, if lower antibody concentrations are required for specific therapeutic interventions or when treating patients of lower body weight including children. Suitable concentrations can be 25 mg/ml or 10 mg/ml. Alternatively, the original formulation may be produced with such a lower concentration.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three or four domains, depending on the isotype, $C_H1$, $C_H2$, $C_H3$ and $C_H4$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of BAFFR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and $C_H1$ domains; a F(ab)$_2$ fragment, a bivalent fragment comprising two Fab fragments linked by a disulfide bridge at the hinge region; a Fd fragment consisting of the $V_H$ and $C_H1$ domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities, e.g., an isolated antibody that specifically binds human BAFFR is substantially free of antibodies that specifically bind antigens other than BAFFR. An isolated antibody that specifically binds BAFFR may, however, have cross-reactivity to other antigens, such as BAFFR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The structures and locations of immunoglobulin variable domains, e.g., CDRs, may be defined using well known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; Al Lazikani et al. (1997) J. Mol. Bio. 273:927 948). Throughout this specification, the complementarity determining region ("CDR") is defined according to the Kabat definition with the exception of CDRH 1 which is the stretch of amino acids defined by a combination of both Kabat and Chothia definitions for this CDR.

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgA, IgD, IgE and IgG such as IgG1, IgG2, IgG3 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to BAFFR polypeptide" or an "anti-BAFFR antibody" refers to an antibody that binds to human BAFFR polypeptide of SEQ ID NO: 13 with a $K_D$ of 100 nM or less, 10 nM or less, 1 nM or less. An antibody that "cross-reacts with an antigen other than BAFFR" refers to an antibody that binds that antigen with a $K_D$ of $0.5 \times 10^{-8}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a Kg of $5-10 \times 10^{-8}$ M or $1 \times 10^{-7}$ M or greater. In certain embodiments, such antibodies that do not cross-react with the antigen exhibit essentially undetectable binding against these proteins in standard binding assays.

In one embodiment, a high concentration of an anti-BAFFR antibody in the aqueous pharmaceutical composition of the invention is at least 50 mg/ml. In one embodiment, a high concentration is at least 100 mg/ml. In one embodiment, a high concentration is at least 150 mg/ml. In one embodiment, a high concentration is at least 200 mg/ml. In one embodiment, a high concentration is at least 250 mg/ml. In one embodiment, a high concentration is at least 300 mg/ml.

In one embodiment, the aqueous pharmaceutical composition of the invention comprises between 50 mg/ml and 300 mg/ml of an anti-BAFFR antibody, for example, MOR6654, especially MOR6654B.

In one embodiment, the aqueous pharmaceutical composition of the invention comprises between 75 mg/ml and 250 mg/ml of an anti-BAFFR antibody, for example, MOR6654, especially MOR6654B.

In one embodiment, the aqueous pharmaceutical composition of the invention comprises between 100 mg/ml and 250 mg/ml of an anti-BAFFR antibody, for example, MOR6654, especially MOR6654B.

In one embodiment, the aqueous pharmaceutical composition of the invention comprises between 100 mg/ml and 200 mg/ml of an anti-BAFFR antibody, for example, MOR6654, especially MOR6654B.

In one embodiment, the aqueous pharmaceutical composition of the invention comprises 150 mg/ml of an anti-BAFFR antibody, for example, MOR6654, especially MOR6654B.

In one embodiment, the aqueous pharmaceutical composition of the invention comprises about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, about 200 mg/ml, about 210 mg/ml, about 220 mg/ml, about 230 mg/ml, about 240 mg/ml, about 250 mg/ml or about 300 mg/ml of an anti-BAFFR antibody, for example, MOR6654, especially MOR6654B.

Furthermore, the aqueous pharmaceutical compositions are stable such that, even after storage for 4 weeks at 2-8° C., less than 5%, 4%, 3%, 2%, 1%, 0.05% or 0.01% of the total anti-BAFFR antibody is aggregated as measured by SEC-HPLC.

The aqueous pharmaceutical compositions may include, in addition to the anti-BAFFR antibody, further components such as one or more of the following: (i) a stabilizer; (ii) a buffering agent; (iii) a surfactant; and (iv) a free amino acid. Inclusion of each of such additional components can give compositions with low aggregation of the anti-BAFFR antibody.

Suitable stabilizer for use with the invention can act, e.g., as viscosity enhancing agents, bulking agents, solubilizing agents, and/or the like. The stabilizer can be ionic or non ionic (e.g. sugars). As sugars they include, but are not limited to, monosaccharides, e.g., fructose, maltose, galactose, glucose, D-mannose, sorbose and the like; disaccharides, e.g. lactose, sucrose, trehalose, cellobiose, and the like; polysaccharides, e.g. raffinose, melezitose, maltodextrins, dextrans, starches, and the like; and alditols, such as mannitol, xylitol, maltitol, lactitol, xylitol sorbitol (glucitol) and the like. For example, the sugar may be sucrose, trehalose, raffinose, maltose, sorbitol or mannitol. The sugar may be a sugar alcohol or an amino sugar. Sucrose is particularly useful. As ionic stabilizer they include salts such as NaCl or amino acid components such as arginine-HCl.

Suitable buffering agents for use with the invention include, but are not limited to, organic acid salts such as salts of citric acid, ascorbic acid, gluconic acid, carbonic acid, tartaric acid, succinic acid, acetic acid or phtalic acid; Tris, thomethamine hydrochloride, or phosphate buffer. In addition, amino acid components can also be used as buffering agent. Such amino acid component includes without limitation glycine and histidine. A histidine buffer is particularly useful.

The aqueous pharmaceutical compositions include such buffering agent or pH adjusting agent to provide improved pH control. In one embodiment, an aqueous pharmaceutical composition of the invention has a pH between 5.0 and 8.0, between 5.0 and 7.0, between 6.0 and 8.0, or between 6.0 and 7.0. In a specific embodiment, an aqueous pharmaceutical composition of the invention has a pH of about 6.5.

As used herein, the term "surfactant" herein refers to organic substances having amphipathic structures; i.e., they are composed of groups of opposing solubility tendencies, typically an oil-soluble hydrocarbon chain and a water-soluble ionic group. Surfactants can be classified, depending on the charge of the surface-active moiety, into anionic, cationic and dispersing agents for various pharmaceutical compositions and preparations of biological materials.

Suitable surfactants for use with the invention include, but are not limited to, non-ionic surfactants, ionic surfactants and zwitterionic surfactants. Typical surfactants for use with the invention include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g. sodium polyoxyethylene lauryl sulfate), and $C_1$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12}$-$C_{18}$ fatty acids. A composition may include one or more of these surfactants. Preferred surfactants are polyoxyethylene sorbitan fatty acid esters e.g. polysorbate 20, 40, 60 or 80. Polysorbate 80 (Tween 80) is particularly useful.

Suitable free amino acids for use with the invention include, but are not limited to, arginine, lysine, histidine, ornithine, isoleucine, leucine, alanine, glycine glutamic acid or aspartic acid. The inclusion of a basic amino acid is preferred i.e. arginine, lysine and/or histidine. If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g. a hydrochloride salt, such as arginine-HCl.

When present, components (i) to (iv) will be at a concentration sufficient to maintain the anti-BAFFR antibody in a form which is active and soluble after either (i) lyophilisation and storage and reconstitution (for lyophilisates), or (ii) conditioning in dosing units and storage (for liquid formulations).

Thus a sugar may be present in the aqueous pharmaceutical composition of the invention, e.g. after reconstitution of a lyophilisate in water, at a concentration of between 3 and 400 mM e.g. 50-300 mM, 200-300 mM, 250-300 mM. A concentration of 270 mM sucrose is useful.

A buffering agent may be present in the aqueous pharmaceutical composition of the invention, e.g. after reconstitution of a lyophilisate in water, at a concentration of between 1 and 60 mM e.g. 10-40 mM, 15-30 mM, 15-25 mM. A concentration of 21 mM histidine buffer is useful.

A surfactant may be present in the aqueous pharmaceutical composition of the invention, e.g. after reconstitution of a lyophilisate in water, at a concentration of up to 0.2% (by volume) e.g. 0.01-0.1%, 0.03-0.08%, 0.04-0.08%. A concentration of 0.06% polysorbate 80 or polysorbate 20 is useful.

A free amino acid may be present in the aqueous pharmaceutical composition of the invention, e.g. after reconstitution of a lyophilisate in water, at a concentration of between 2 and 100 mM e.g. 10-80 mM, 20-70 mM, 30-60 mM, 40-60 mM. A concentration of 51 mM arginine-HCl or 60 mM glycine-HCl is useful.

A formulation containing histidine buffer, sucrose and polysorbate 80 has been shown to be suitable for lyophilisation of antibody MOR6654B at a concentration of at least 150 mg/ml after reconstitution.

In one embodiment the aqueous pharmaceutical composition consists of 150 mg/ml MOR6654 or MOR6654B, 21 mM histidine, 270 mM sucrose and 0.06% polysorbate 80.

In one embodiment the aqueous pharmaceutical composition consists of 150 mg/ml MOR6654 or MOR6654B, 21 mM histidine, 270 mM sucrose, 0.06% polysorbate 80 and 60 mM glycine-HCl.

In one embodiment the aqueous pharmaceutical composition consists of 150 mg/ml MOR6654 or MOR6654B, 21 mM histidine, 270 mM sucrose, 0.06% polysorbate 80 and 51 mM arginine-HCl.

In one embodiment the aqueous pharmaceutical composition consists of 200 mg/ml MOR6654 or MOR6654B, 21 mM histidine, 270 mM sucrose, 0.06% polysorbate 80 and 51 mM arginine-HCl.

In one embodiment the aqueous pharmaceutical composition consists of 75 mg/ml MOR6654 or MOR6654B, 21 mM histidine, 270 mM sucrose, 0.06% polysorbate 80 and 51 mM arginine-HCl.

Other contemplated excipients, which may be utilized in the aqueous pharmaceutical compositions of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4$^{th}$ edition, Rowe et al., Eds., American Pharmaceuticals Association (2003); and Remington: the Science and Practice of Pharmacy, 21$^{th}$ edition, Gennaro, Ed., Lippincott Williams & Wilkins (2005).

The aqueous pharmaceutical compositions of the invention may include further active ingredients in addition to the anti-BAFFR antibody. Further pharmacological agents may include, for instance, chemotherapeutic compounds.

Lyophilisates

Techniques for lyophilisation of antibodies are well known in the art e.g. see John F. Carpenter and Michael J. Pikal, 1997 (*Pharm. Res.* 14, 969-975); Xialin (Charlie) Tang and Michael J. Pikal, 2004 (*Pharm. Res.* 21, 191-200). For example, the monoclonal antibody products SYNAGIS™, REMICADE™, RAPTIVA™, SIMULECT™, XOLAIR™ and HERCEPTIN™ are supplied as lyophilisates. These antibodies are reconstituted to various final concentrations e.g. SIMULECT™ is reconstituted to a concentration of 4 mg/ml antibody, REMICADE™ is reconstituted to a concentration of 10 mg/ml, HERCEPTIN™ to 21 mg/ml, SYNAGIS™ and RAPTIVAT™ to 100 mg/ml, and XOLAIR™ to 125 mg/ml.

Pre-Lyophilisates, Lyophilisates and Aqueous Reconstitution

Before a lyophilisate can be administered to a patient it should be reconstituted with an aqueous reconstituent. This step permits antibody and other components in the lyophilisate to re-dissolve to give a solution which is suitable for injection to a patient.

The volume of aqueous material used for reconstitution dictates the concentration of the antibody in a resulting pharmaceutical composition. Reconstitution with a smaller volume of reconstituent than the pre-lyophilisation volume provides a composition which is more concentrated than before lyophilisation. The reconstitution factor (volume of formulation after lyophilization:volume of formulation before lyophilization) may be from 1:0.5 to 1:6. A reconstitution factor of 1:3 is useful. As mentioned above, lyophilisates of the invention can be reconstituted to give aqueous compositions with an anti-BAFFR antibody concentration of at least 50 mg/ml, 100 mg/ml, 150 mg/ml. 200 mg/ml, 250 mg/ml or 300 mg/ml, and the volume of reconstituent will be selected accordingly. If required, the reconstituted formulation can be diluted prior to administration to a patient as appropriate to deliver the intended dose.

Typical reconstituents for lyophilized antibodies include sterile water or buffer, optionally containing a preservative. If the lyophilisate includes a buffering agent then the reconstituent may include further buffering agent (which may be the same as or different from the lyophilisate's buffering agent) or it may instead include no buffering agent (e.g. WFI (water for injection), or physiological saline).

When present, components (i) to (iv) will be at a pre-lyophilisation concentration sufficient to maintain the anti-BAFFR antibody in a form which is active and soluble after storage (under normal conditions) and reconstitution. The components will also be present after reconstitution.

Thus a sugar, such as sucrose or trehalose, may be present before lyophilisation at a concentration of between 3 and 300 mM e.g. 15-200 mM, 30-150 mM, 80-100 mM. A concentration of 90 mM sucrose is useful. A buffering agent, such as histidine, may be present before lyophilisation at a concentration of between 1 and 60 mM e.g. 3-30 mM, 5-20 mM, 5-15 mM. A concentration of 7 mM histidine buffer is useful. A surfactant, such as polysorbate 80 or polysorbate 20 may be present before lyophilisation at a concentration of up to 0.2% (by volume) e.g. 0.01-0.1%, 0.01-0.08%, 0.01-0.04%. A concentration of 0.02% polysorbate 80 or polysorbate 20 is useful. A free amino acid, such as arginine or glycine, may be present before lyophilisation at a concentration of between 2 and 80 mM e.g. 3-50 mM, 6-30 mM, 10-25 mM, 15-20 mM. A concentration of 17 mM arginine-HCl or 20 mM glycine-HCl is useful. The anti-BAFFR antibody is present before lyophilization at a concentration of between 20 mg/ml and 120 mg/ml, e.g. 20 mg/ml, 30 mg/ml, 40 mg/ml, 50 mg/ml, 60 mg/ml, 66.6 mg/ml, 70 mg/ml, 80 mg/ml, 90 mg/ml, 100 mg/ml, 110 mg/ml, or 120 mg/ml. A concentration of 50 mg/ml is useful.

The pre-lyophilisate of the invention has a pH between 5.0 and 8.0, between 5.0 and 7.0, between 6.0 and 8.0, or between 6.0 and 7.0. In a specific embodiment, the pre-lyophilisate of the invention has a pH of about 6.5.

In one embodiment the pre-lyophilisate of the invention has a molar ratio of sucrose:antibody of 270:1 and a molar ratio of histidine:antibody of 21:1.

In one embodiment the pre-lyophilisate of the invention has a molar ratio of sucrose:antibody of 270:1, a molar ratio of histidine:antibody of 21:1, and a molar ratio of arginine-HCl:antibody of 51:1.

In one embodiment the pre-lyophilisate of the invention has a molar ratio of sucrose:antibody of 270:1, a molar ratio of histidine:antibody of 21:1, and a molar ratio of glycine-HCl:antibody of 60:1.

In one embodiment the pre-lyophilisate of the invention has a molar ratio of sucrose:antibody of 203:1, a molar ratio of histidine:antibody of 16:1, and a molar ratio of arginine-HCl:antibody of 38:1.

A formulation containing histidine buffer, sucrose, polysorbate 80 and, optionally arginine or glycine has been shown to be suitable for lyophilisation of antibody MOR6654B. After reconstitution, the components of the lyophilisate may be present at a concentration of the aqueous pharmaceutical compositions as described hereinbefore.

Target Diseases and Disorders

The aqueous pharmaceutical compositions of the invention comprising anti-BAFFR antibodies can be used to treat, ameliorate or prevent a variety of diseases or disorders. Pharmaceutical compositions comprising anti-BAFFR antibodies are particularly useful to treat BAFFR related disorders such as autoimmune disorders, e.g., systemic lupus erythematosus, Pemphigus vulgaris, rheumatoid arthritis, multiple sclerosis and B cell neoplasms such as acute lymphoblastic leukemia (ALL) and B-cell chronic lymphocytic leukemia (CLL).

As used herein, "a BAFFR-related disorder" includes conditions associated with or characterized by aberrant BLyS levels and/or diseases or conditions that can be treated by depleting or killing B cells. These includes, without limitations, inflammatory conditions, autoimmune diseases, severe infections, and organ or tissue transplant rejection. These further include B-cell neoplasms.

For example, the aqueous pharmaceutical compositions of the invention comprising anti-BAFFR antibodies may be used for the treatment, amelioration or prevention of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis. Further, the aqueous pharmaceutical compositions of the invention are useful in solid organ transplantation and in antibody-mediated acute and chronic transplant rejection.

The aqueous pharmaceutical compositions of the invention comprising anti-BAFFR antibodies are useful for the treatment, prevention, or amelioration of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankylosing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, scleroderma, vasculitis such as cryoglobulinemia, large vessel vasculitides such as giant cell arteritis, polymyalgia rheumatica, necrotizing vasculitides, including anti-neutrophil cytoplasmic antibody-associated vasculitis, Takayasu's arteritis, polyarteritis nodosa, Henoch-Schonlein purpura, and Churg-Strauss syndrome, IgM mediated neuropathy, seronegative spondarthritis, opsoclonus myoclonus syndrome, Wegener granulomatosis, dermatomyositis, anti-neutrophil cytoplasmatic autoantibody (ANCA) vasculitis, chronic active hepatitis, myasthenia gravis, psoriasis, Steven-Johnson syndrome, pemphigus vulgaris, pemphigus foliacius, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), acute nephritic lupus, tumors, inflammatory disease of skin and cornea, myositis, loosening of bone implants, metabolic disorders, such as atherosclerosis, diabetes, and dislipidemia.

The aqueous pharmaceutical compositions of the invention may also be useful in preventing, ameliorating or treating B-cell neoplasms. Examples of such diseases and conditions include, but are not limited to, B-cell Non-Hodgkin's lymphomas, such as small lymphocytic lymphoma, lymphoplasmacytoid lymphoma, mantle cell lymphoma, follicular lymphoma, mucosa-associated lymphoid tissue lymphoma, diffuse large cell lymphoma, and Burkitt's lymphoma; acute lymphoblastic leukemia (ALL), precursor B-lymphoblastic leukemia; B-cell chronic lymphocytic leukemia (CLL), and multiple myeloma. Other B-cell neoplasms are encompassed within the scope of the invention.

Patient Administration

A pharmaceutical composition of the invention can be administered to a patient. Administration will typically be via a syringe. Thus the invention provides a delivery device (e.g. a syringe) including a pharmaceutical composition of the invention (e.g., pre-filled syringe). Patients will receive an effective amount of the anti-BAFFR antibody as the principal active ingredient i.e. an amount that is sufficient to treat, ameliorate, or prevent the disease or disorder in question. Therapeutic effects may also include reduction in physical symptoms. The optimum effective amount and concentration of antibody for any particular subject will depend upon various factors, including the patient's age size health and/or gender, the nature and extent of the condition, the activity of the particular antibody, the rate of its clearance by the body, and also on any possible further therapeutic(s) administered in combination with the antibody. The effective amount delivered for a given situation can be determined within the judgment of a clinician. For purposes of the present invention, an effective dose may be from about 0.005 mg/kg to about 50 mg/kg, or about 0.05 mg/kg to about 10 mg/kg. Known antibody-based pharmaceuticals provide guidance in this respect e.g. HERCEPTIN™ is administered with an initial loading dose of 4 mg/kg body weight and a weekly maintenance dose of 2 mg/kg body weight; RITUXAN™ is administered weekly at 375 mg/m$^2$; SYNAGIS™ is administered intramuscularly at 15 mg/kg body weight; etc.

The invention provides a method for delivering a monoclonal antibody to a mammal, comprising a step of administering to the patient a pharmaceutical composition of the invention.

The invention also provides a method for delivering a monoclonal antibody to a mammal, comprising steps of: (i) reconstituting a lyophilisate of the invention to give an aqueous formulation, and (ii) administering the aqueous formulation to the patient. Step (ii) ideally takes place within 24 hours of step (i) e.g. within 12 hours, within 6 hours, within 3 hours, or within 1 hour.

The invention also provides formulations of the invention for use as medicaments e.g. for use in delivering an antibody to a mammal, or for use in treating, preventing or ameliorating one or more of the diseases and disorders described above.

The mammal is preferably a human but may also be, for example, a horse or a cow or a dog or a cat. The antibodies will ideally be chosen to match the target species e.g. a human antibody for human administration, an equine antibody for horses, a canine antibody for dogs, etc. If native host antibodies are not available then transfer of antibody specificity from one species to another can be achieved by transfer of CDR residues (and typically, in addition, one or more framework residues) from a donor antibody into a recipient framework from the host species e.g. as in humanization. Equinized, bovinized, caninized and felinized antibodies are known in the art. The antibody will bind to BAFFR from the target species, but it may also cross-react with BAFFR from other species.

Dosage can be by a single dose schedule or a multiple dose schedule.

Ingredients for forming compositions of the invention (e.g. lyophilisates and reconstituents) may be supplied in hermetically-sealed containers.

The Anti-BAFFR Antibody

The invention concerns the formulation of anti-BAFFR antibodies and more specifically MOR6654 and MOR6654B.

One suitable antibody that can be comprised in the pharmaceutical compositions of the invention is the human recombinant antibody MOR6654, structurally characterized as further described below. The $V_H$ amino acid sequence of such isolated anti-BAFFR antibody is shown in SEQ ID NO: 1. The $V_L$ amino acid sequence of such isolated anti-BAFFR antibody is shown in SEQ ID NO: 2. An example of the full length heavy chain amino acid sequence of such isolated anti-BAFFR antibody is shown in SEQ ID NO: 9. An example of the full-length light chain amino acid sequence of such isolated anti-BAFFR antibody is shown in SEQ ID NO: 10. Another example of heavy and light chain amino acid sequences of such isolated anti-BAFFR antibodies are those encoded by the nucleotide sequences of SEQ ID NO: 11 and SEQ ID NO: 12 respectively. Another example of heavy and light chain amino acid sequences of antibodies are those encoded by corresponding DNA sequences contained in plasmid pBW510 as deposited by Novartis Pharma AG, Forum 1, CH-4002 Basel, Switzerland, at DSMZ on Apr. 29, 2009 with accession number DSM22542.

Other anti-BAFFR antibodies that can be used for preparing the pharmaceutical compositions of the invention include anti-BAFFR antibodies, with amino acids that have been mutated by amino acid deletion, insertion or substitution, yet have no more than 1, 2, 3, 4 or 5 amino acid deletion, insertion or substitution in either the heavy or light chain regions described above. In a specific embodiment, such amino acid changes appear only within the framework and/or constant regions and the CDR regions are 100% identical to the heavy chain CDR1, CDR2 and CDR3 regions of SEQ ID NO: 3, 4 and 5 and to the light chain CDR1, CDR2 and CDR3 regions of SEQ ID NO: 6, 7, and 8 respectively. In one more specific embodiment, the changes that have been made are only conservative amino acid substitutions outside of the CDR regions.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues outside of the CDR regions of an anti-BAFFR antibody, can be replaced with other amino acid residues from the same side chain family, and the altered antibody can be tested for retained function, in particular the same binding properties to BAFFR.

Antibodies may typically be glycosylated. N-linked glycans attached to the $C_H2$ domain of a heavy chain, for instance, can influence C1q and FcR binding, and aglycosylated antibodies may have lower or different affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the antibody-dependent cell-mediated cytotoxicity (ADCC) ability of antibodies. Such carbohydrate modifications can be accomplished by, for example, expressing the antibody in a host cell with altered glycosylation machinery. Cells with an altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the anti-BAFFR antibodies that are included in the pharmaceutical compositions of the invention are produced by recombinant expression in a cell line which exhibit hypofucosylation or non-fucosylation pattern, for example, a mammalian cell line with deficient expression of the FUT8 gene encoding fucosyltransferase.

As used herein, the term MOR6654 encompasses any type of glycosyation pattern. In a specific embodiment, the pharmaceutical compositions comprises an anti-BAFFR antibody consisting of MOR6654 as produced in a cell line which exhibits a hypofucosylation or non-fucosylation pattern, such as MOR6654B, which exhibit nonfucosylation pattern (devoid of fucosyl residues). PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, RL et al., 2002J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues (www.eurekainc.com/about_us/companyoverview.html). Alternatively, the anti-BAFFR antibodies can be produced in yeasts or filamentous fungi engineered for mammalian-like glycosylation pattern and capable of producing antibodies lacking fucose as glycosylation pattern (see for example EP1297172B1).

Another modification of the anti-BAFFR antibodies herein that is contemplated by the invention is pegylation. An antibody can be pegylated to, for example, increase the biological (e.g., serum) half-life of the antibody. To pegylate an antibody, the antibody, or fragment thereof, typically may be reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer).

As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Any other natural or non-natural post-translational modification of anti-BAFFR antibodies (e.g. MOR6654) is further contemplated as specific embodiments of anti-BAFFR antibodies that could be used for preparing the pharmaceutical compositions of the invention.

Antibodies can be prepared in a form free from products with which they would naturally be associated. Contaminant components of an antibody's natural environment include materials such as enzymes, hormones, or other host cell proteins.

EXAMPLES

Preparing Anti-BAFFR Antibodies

Antibody MOR6654 binds specifically to BAFFR and is also described in reference WO2010/007082. It is a human IgG1 kappa antibody obtained via phage display. Its heavy and light chains consist of SEQ ID NOs: 9 and 10. The Tables 1 and 2 below summarize the sequence characteristics of MOR6654.

This antibody may be produced in mammalian host cells, such as, a CHO cell line transfected with expression vectors carrying heavy and light chain coding sequences under suitable expression promoters.

This antibody is preferably produced in a mammalian cell line, e.g. a CHO cell line, wherein the gene encoding fucosyltransferase (FUT8 gene) has been inactivated. The resulting antibody is non-fucosylated and designated here as MOR6654B.

TABLE 1

Brief description of the sequences listed in the sequence listing of Table 2

| SEQ ID NO: | Description of the sequence |
|---|---|
| 1 | Amino acid sequence of the variable region ($V_H$) of the heavy chain of MOR6654 |
| 2 | Amino acid sequence of the variable region ($V_L$) of the light chain of MOR6654 |
| 3 | Amino acid sequence of HCDR1 of MOR6654 |
| 4 | Amino acid sequence of HCDR2 of MOR6654 |
| 5 | Amino acid sequence of HCDR3 of MOR6654 |
| 6 | Amino acid sequence of LCDR1 of MOR6654 |
| 7 | Amino acid sequence of LCDR2 of MOR6654 |
| 8 | Amino acid sequence of LCDR3 of MOR6654 |
| 9 | Amino acid sequence of the full length heavy chain of MOR6654 |
| 10 | Amino acid sequence of the full length light chain of MOR6654 |
| 11 | Nucleotide sequence encoding SEQ ID NO: 1 |
| 12 | Nucleotide sequence encoding SEQ ID NO: 2 |
| 13 | Human BAFFR amino acid sequence |
| 14 | Full length nucleotide sequence (including leader sequence and constant part) of MOR6654 heavy chain; nt 1-57 = leader; nt 58-429 = VH; nt 430-1419 = constant region (hIgG1) |
| 15 | Full length nucleotide sequence (including leader sequence and constant part) of MOR6654 light chain; nt 1-60 = leader; nt 61-384 = VL; nt 385-705 = constant region (hkappa) |

TABLE 2

Sequence listing

| SEQ ID NO: | Amino acid or Nucleotide Sequence |
|---|---|
| 1 | QVQLQQSGPGLVKPSQTLSLICAISGDSVSSNSAAWGWIRQSPGRGLEWLGRIYYRSKWYNSYAVSVKSRITINPDTSKNQFSLQLNSVTPEDTAVYYCARYDWVPKIGVFDSWGQGTLVTVSS |
| 2 | DIVLTQSPATLSLSPGERATLSCRASQFISSSYLSWYQQKPGQAPRLLIYGSSSRATGVPARFSGSGSGTDFTLTISSLEPEDFAVYYCQQLYSSPMTFGQGTKVEIK |

TABLE 2-continued

Sequence listing

| SEQ ID NO: | Amino acid or Nucleotide Sequence |
|---|---|
| 3 | GDSVSSNSAAWG |
| 4 | RIYYRSKWYNSYAVSVKS |
| 5 | YDWVPKIGVFDS |
| 6 | RASQFISSSYLS |
| 7 | GSSSRAT |
| 8 | QQLYSSPMT |
| 9 | QVQLQQSGPGLVKPSQTLSLTCAISGDSVSSNSAAWGWIRQSPGRGLEWLG RIYYRSKWYNSYAVSVKSRITINPDTSKNQFSLQLNSVTPEDTAVYYCARYD WVPKIGVFDSWGQGTLVTVSSASTKGPSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCDKTHTCPPCPAPELLGGPSVFLFPPKPKDTLM ISRTPEVTCVVVDVSHEDPEVKFNINYVDGVEVHNAKTKPREEQYNSTYRVV SVLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 10 | DIVLTQSPATLSLSPGERATLSCRASQFISSSYLSVVYQQKPGQAPRLLIYGSS SRATGVPARFSGSGSGTDFTLTISSLEPEDFAVYYCQQLYSSPMTFGQGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC |
| 11 | CAGGTGCAGCTGCAGCAGAGCGGCCCAGGCCTGGTCAAGCCCTCTCAGA CCCTGTCACTGACCTGCGCCATTTCAGGCGACAGCGTGAGCAGCAACAG CGCCGCCTGGGGCTGGATCAGGCAGAGCCCCGGTAGGGGCCTGGAATG GCTGGGCAGGATCTACTACAGGTCCAAGTGGTACAACAGCTACGCCGTG AGCGTGAAGAGCAGGATCACCATCAACCCTGACACCAGCAAGAACCAGTT CTCACTGCAGCTCAACAGCGTGACCCCCGAGGACACCGCCGTGTACTAC TGCGCCAGATACGACTGGGTGCCCAAGATCGGCGTGTTCGACAGCTGGG GCCAGGGCACCCTGGTGACCGTGTCAAGC |
| 12 | GATATCGTGCTGACACAGAGCCCCGCCACCCTGAGCCTGAGCCCAGGCG AGAGGGCCACCCTGTCCTGCAGGGCCAGCCAGTTTATCAGCAGCAGCTA CCTGTCCTGGTATCAGCAGAAGCCCGGCCAGGCCCCTAGACTGCTGATC TACGGCAGCTCCTCTCGGGCCACCGGCGTGCCCGCCAGGTTCAGCGGC AGCGGCTCCGGCACCGACTTCACCCTGACAATCAGCAGCCTGGAGCCCG AGGACTTCGCCGTGTACTACTGCCAGCAGCTGTACAGCTCACCCATGACC TTCGGCCAGGGCACCAAGGTGGAGATCAAG |
| 13 | MRRGPRSLRGRDAPAPTPCVPAECFDLLVRHCVACGLLRTPRPKPAGASSP APRTALQPQESVGAGAGEAALPLPGLLFGAPALLGLALVLALVLVGLVSWRR RQRRLRGASSAEAPDGDKDAPEPLDKVIILSPGISDATAPAWPPPGEDPGTT PPGHSVPVPATELGSTELVTTKTAGPEQQ |
| 14 | ATGGCCTGGGTGTGGACCCTGCCCTTCCTGATGGCCGCTGCCCAGTCAG TGCAGGCCCAGGTGCAGCTGCAGCAGAGCGGCCCAGGCCTGGTCAAGC CCTCTCAGACCCTGTCACTGACCTGCGCCATTTCAGGCGACAGCGTGAG CAGCAACAGCGCCGCCTGGGGCTGGATCAGGCAGAGCCCCGGTAGGGG CCTGGAATGGCTGGGCAGGATCTACTACAGGTCCAAGTGGTACAACAGC TACGCCGTGAGCGTGAAGAGCAGGATCACCATCAACCCTGACACCAGCA AGAACCAGTTCTCACTGCAGCTCAACAGCGTGACCCCCGAGGACACCGC CGTGTACTACTGCGCCAGATACGACTGGGTGCCCAAGATCGGCGTGTTC GACAGCTGGGGCCAGGGCACCCTGGTGACCGTGTCAAGCGCCAGCACC AAGGGCCCCAGCGTGTTCCCCCTGGCCCCCAGCAGCAAGAGCACCAGC GGCGGCACAGCCGCCCTGGGCTGCCTGGTGAAGGACTACTTCCCCGAG CCCGTGACCGTGTCCTGGAACAGCGGAGCCCTGACCTCCGGCGTGCACA CCTTCCCCGCCGTGCTGCAGAGCAGCGGCCTGTACAGCCTGTCCAGCGT GGTGACAGTGCCCAGCAGCAGCCTGGGCACCCAGACCTACATCTGCAAC GTGAACCACAAGCCCAGCAACACCAAGGTGGACAAGAGAGTGGAGCCCA AGAGCTGCGACAAGACCCACACCTGCCCCCCCTGCCCAGCCCCAGAGCT GCTGGGCGGACCCTCCGTGTTCCTGTTCCCCCCCAAGCCCAAGGACACC CTGATGATCAGCAGGACCCCCGAGGTGACCTGCGTGGTGGTGGACGTGA GCCACGAGGACCCAGAGGTGAAGTTCAACTGGTACGTGGACGGCGTGGA GGTGCACAACGCCAAGACCAAGCCCAGAGAGGAGCAGTACAACAGCACC TACAGGGTGGTGTCCGTGCTGACCGTGCTGCACCAGGACTGGCTGAACG GCAAGGAATACAAGTGCAAGGTCTCCAACAAGGCCCTGCCAGCCCCCAT CGAAAAGACCATCAGCAAGGCCAAGGGCCAGCCACGGGAGCCCCAGGT GTACACCCTGCCCCCCTCCCGGGAGGAGATGACCAAGAACCAGGTGTCC |

TABLE 2-continued

Sequence listing

| SEQ ID NO: | Amino acid or Nucleotide Sequence |
|---|---|
|  | CTGACCTGTCTGGTGAAGGGCTTCTACCCCAGCGACATCGCCGTGGAGT GGGAGAGCAACGGCCAGCCCGAGAACAACTACAAGACCACCCCCCCAGT GCTGGACAGCGACGGCAGCTTCTTCCTGTACAGCAAGCTGACCGTGGAC AAGTCCAGGTGGCAGCAGGGCAACGTGTTCAGCTGCAGCGTGATGCACG AGGCCCTGCACAACCACTACACCCAGAAGAGCCTGAGCCTGTCCCCCGG CAAG |
| 15 | ATGAGCGTGCTGACCCAGGTGCTGGCTCTGCTGCTGCTGTGGCTGACCG GCACCAGATGCGATATCGTGCTGACACAGAGCCCCGCCACCCTGAGCCT GAGCCCAGGCGAGAGGGCCACCCTGTCCTGCAGGGCCAGCCAGTTTATC AGCAGCAGCTACCTGTCCTGGTATCAGCAGAAGCCCGGCCAGGCCCCTA GACTGCTGATCTACGGCAGCTCCTCTCGGGCCACCGGCGTGCCCGCCAG GTTCAGCGGCAGCGGCTCCGGCACCGACTTCACCCTGACAATCAGCAGC CTGGAGCCCGAGGACTTCGCCGTGTACTACTGCCAGCAGCTGTACAGCT CACCCATGACCTTCGGCCAGGGCACCAAGGTGGAGATCAAGCGTACGGT GGCCGCTCCCAGCGTGTTCATCTTCCCCCCCAGCGACGAGCAGCTGAAG AGCGGCACCGCCAGCGTGGTGTGCCTGCTGAACAACTTCTACCCCCGGG AGGCCAAGGTGCAGTGGAAGGTGGACAACGCCCTGCAGAGCGGCAACA GCCAGGAGAGCGTCACCGAGCAGGACAGCAAGGACTCCACCTACAGCCT GAGCAGCACCCTGACCCTGAGCAAGGCCGACTACGAGAAGCATAAGGTG TACGCCTGCGAGGTGACCCACCAGGGCCTGTCCAGCCCCGTGACCAAGA GCTTCAACAGGGGCGAGTGC |

Examples of Formulations

A high concentration lyophilized or liquid formulation of MOR6654B was desired and so formulation studies were performed. A lyophilized formulation comprising a sugar, a buffering agent and a surfactant was stable and could maintain high antibody concentrations after reconstitution.

Three formulations (F1, F2, F3) of MOR6654B at 150 mg/vial and one formulation at 200 mg/vial (F3b) were evaluated for stability. Formulations F1, F2 and F3 had, prior to lyophilisation, 50 mg/ml MOR6654B at pH 6.5, and formulation F3b 66.6 mg/ml at pH 6.5. The four formulations had a fill volume of 3.6 ml and included buffer, sugar, surfactant and free amino acid as follows in Table 3:

TABLE 3

Examples of formulations

|  | MOR6654B | Buffer | Sugar | Surfactant | Amino acid |
|---|---|---|---|---|---|
| F1 | 50 mg/ml | 7 mM histidine | 90 mM sucrose | 0.02% polysorbate 80 | — |
| F2 | 50 mg/ml | 7 mM histidine | 90 mM sucrose | 0.02% polysorbate 80 | 20 mM glycine-HCl |
| F3 | 50 mg/ml | 7 mM histidine | 90 mM sucrose | 0.02% polysorbate 80 | 17 mM arginine-HCl |
| F3b | 66.6 mg/ml | 7 mM histidine | 90 mM sucrose | 0.02% polysorbate 80 | 17 mM arginine-HCl |

The lyophilisates were reconstituted with WFI (1 ml) to give a reconstituted volume of 1.2 ml (20% overage; ⅓ the original aqueous volume). The reconstituted compositions were as in Table 4:

TABLE 4

Examples of formulations

|  | MOR6654B | Buffer | Sugar | Surfactant | Amino acid |
|---|---|---|---|---|---|
| F1 | 150 mg/ml | 21 mM histidine | 270 mM sucrose | 0.06% polysorbate 80 | — |
| F2 | 150 mg/ml | 21 mM histidine | 270 mM sucrose | 0.06% polysorbate 80 | 60 mM glycine-HCl |
| F3 | 150 mg/ml | 21 mM histidine | 270 mM sucrose | 0.06% polysorbate 80 | 51 mM arginine-HCl |
| F3b | 200 mg/ml | 21 mM histidine | 270 mM sucrose | 0.06% polysorbate 80 | 51 mM arginine-HCl |

The lyophilisation cycle used is reported in Table 5.

TABLE 5

The lyophilisation cycle parameters

| Step | Operation | Time [hh:mm] | Shelf temp. | Chamber pressure |
|---|---|---|---|---|
| 1 | Vial loading | As required | 20° C. | Ambient |
| 2 | 5° C. cooling | 00:30 | 5° C. | Ambient |
| 3 | 5° C. hold | 03:00 | 5° C. | Ambient |
| 4 | Freeze ramp | 01:24 | 5° C. to −37° C. | Ambient |
| 5 | Freeze hold | 04:00 | −37° C. | Ambient |
| 6 | Chamber Vacuum | 00:10 | −37° C. | 0.2 mbar[a] |
| 7 | Primary drying ramp | 16:00 | −37° C. to 25° C. | 0.2 mbar[a] |
| 8 | Secondary drying hold | 24:00 | 25° C. | 0.2 mbar[a] |
| 11 | Vial stoppering |  | 25° C. | 850 ± 50 mbar |

[a]Chamber pressure was controlled using sterile filtered nitrogen. The pressure was determined by instruments based on capacitance measurements.

The four reconstituted formulations were tested for stability (i) prior to lyophilisation, (ii) after immediate post-lyophilisation reconstitution, and (iii) after reconstitution following storage at 2-8° C. or 40° C. for four weeks. Stability was evaluated by % impurities as measured by size exclusion—High Pressure Liquid Chromatography (SEC-HPLC), Dynamic Light Scattering (DLS) and visual inspection (assessed after overnight storage at 2-8° C.). The results are shown in Tables 6 to 10 below.

TABLE 6

Aggregation products results from SEC-HPLC

|     | Pre-lyophilisation | Post-lyophilisation | 2-8° C. for 4 weeks | 40° C. for 4 weeks |
| --- | --- | --- | --- | --- |
| F1  | <0.1% | <0.1% | <0.1% | 0.24% |
| F2  | <0.1% | <0.1% | <0.1% | 0.18% |
| F3  | <0.1% | <0.1% | <0.1% | 0.14% |
| F3b | <0.1% | <0.1% | <0.1% | 0.23% |

TABLE 7

Degradation products results from SEC-HPLC

|     | Pre-lyophilisation | Post-lyophilisation | 2-8° C. for 4 weeks | 40° C. for 4 weeks |
| --- | --- | --- | --- | --- |
| F1  | 0.15% | 0.11% | 0.16% | 0.16% |
| F2  | 0.13% | 0.14% | 0.14% | 0.12% |
| F3  | 0.12% | 0.15% | 0.13% | 0.10% |
| F3b | 0.11% | 0.12% | 0.15% | 0.11% |

TABLE 8

Small particles; results for PolyDispensity Index (PDI) from Dynamic Light Scattering

|     | Pre-lyophilisation | Post-lyophllisation | 2-8° C. for 4 weeks | 40° C. for 4 weeks |
| --- | --- | --- | --- | --- |
| F1  | 12.5% | 27.5% | 23.8% | 23.8% |
| F2  | 12.1% | 43.9% | 23.5% | 23.5% |
| F3  | 7.4%  | 19.4% | 17.3% | 16.1% |
| F3b | 7.7%  | 22.8% | 18.3% | 17.8% |

TABLE 9

Small particles; results for particles radius (r · nm) from Dynamic Light Scattering (diluted samples)

|     | Pre-lyophilisation | Post-lyophilisation | 2-8° C. for 4 weeks | 40° C. for 4 weeks |
| --- | --- | --- | --- | --- |
| F1  | 4.1 nm | 2.9 nm | 3.6 nm | 4.0 nm |
| F2  | 4.2 nm | 3.0 nm | 4.0 nm | 4.4 nm |
| F3  | 5.6 nm | 5.5 nm | 5.5 nm | 5.7 nm |
| F3b | 5.7 nm | 5.7 nm | 5.9 nm | 5.7 nm |

TABLE 10

Visual clarity

|     | Pre-lyophilisation | Post-lyophilisation | 2-8° C. for 4 weeks | 40° C. for 4 weeks |
| --- | --- | --- | --- | --- |
| F1  | Clear, no visible particles | Clear, no visible particles | Clear, no visible particles | Clear, no visible particles |
| F2  | Clear, no visible particles | Clear, no visible particles | Clear, no visible particles | Clear, no visible particles |
| F3  | Clear, no visible particles | Clear, no visible particles | Clear, no visible particles | Clear, no visible particles |
| F3b | Clear, no visible particles | Clear, no visible particles | Clear, no visible particles | Clear, no visible particles |

Overall, all the formulation tested showed good results. F3 showed the lowest aggregation of MOR6654B before and after reconstitution, measured by Dynamic Light Scattering (DLS, see Table 8). Based on these results a stability study was performed with formulation F3. The reconstituted F3 formulation was prepared as described above but in a 10 L scale. Table 11 shows the stability results obtained with F3 as measured by SEC-HPLC.

TABLE 11

Stability of F3 as measured by SEC-HPLC

| Storage Conditions | | Purity | Sum of aggregates | Sum of fragments |
| --- | --- | --- | --- | --- |
| Initial analysis | | 99.6 | 0.36 | <0.10 |
| 5° C. | 3 months | 99.5 | 0.44 | <0.10 |
|  | 6 months | 99.5 | 0.45 | <0.10 |
| 25° C./60% RH | 3 months | 99.3 | 0.67 | <0.10 |
|  | 6 months | 99.1 | 0.76 | <0.10 |
| 40° C./75% RH | 3 months | 98.6 | 1.4 | <0.10 |
|  | 6 months | 98.1 | 1.7 | 0.10 |

The invention claimed is:

1. A lyophilized formulation prepared by lyophilizing an aqueous formulation having a pH of 6.5 and comprising
   (i) a hypofucosylated or non-fucosylated anti-BAFF Receptor (anti-BAFFR) antibody wherein the antibody has a concentration of 50 mg/ml, and wherein said anti-BAFFR antibody comprises heavy chain CDR1, CDR2 and CDR3 comprising amino acid sequences of SEQ ID NOs: 3, 4 and 5 respectively, and light chain CDR1, CDR2 and CDR3 comprising amino acid sequences of SEQ ID NOs: 6, 7 and 8,
   (ii) 90 mM sucrose as a stabilizer,
   (iii) 7 mM histidine as a buffering agent,
   (iv) 0.02% polysorbate 80 as a surfactant, and
   (v) 17 mM arginine-HCl.

2. An aqueous pharmaceutical composition obtained by reconstituting the lyophilized formulation of claim 1, wherein the reconstitution factor is between 1:0.5 to 1:6.

3. The aqueous pharmaceutical composition of claim 2, wherein the reconstitution factor is 1:3.

4. A delivery device comprising the aqueous pharmaceutical composition of claim 2.

5. A pre-filled syringe comprising the aqueous pharmaceutical composition of claim 2.

6. A method for delivering a hypofucosylated or non-fucosylated anti-BAFFR antibody to a mammal in need of treatment of a disease or disorder that is mediated by BAFF receptor and that can be treated by killing or depleting B cells, comprising a step of administering to the mammal an aqueous pharmaceutical composition of claim 2.

7. The aqueous pharmaceutical composition of claim 2, wherein the hypofucosylated or non-fucosylated anti-BAFFR antibody comprises a heavy chain region comprising the amino acid sequence of SEQ ID NO: 9 and a light chain region comprising the amino acid sequence of SEQ ID NO: 10.

8. A method for treating a disease or disorder that is mediated by BAFF receptor and that can be treated by killing or depleting B cells, comprising administering to a subject the aqueous pharmaceutical composition of claim 2.

9. The method of claim 8, wherein said disease or disorder that is mediated by BAFF receptor and that can be treated by killing or depleting B cells is selected from the group consisting of autoimmune disease, B cell neoplasm, lymphoma, leukemia, myeloma, rheumatoid arthritis, systemic lupus erythematosus, multiple sclerosis, and Pemphigus vulgaris.

10. The aqueous pharmaceutical composition of claim 2, wherein the hypofucosylated or non-fucosylated anti-BAFFR antibody comprises a $V_H$ domain comprising the amino acid sequence of SEQ ID NO: 1 and a $V_L$ domain comprising the amino acid sequence of SEQ ID NO: 2.

11. The lyophilized formulation of claim 1, wherein the hypofucosylated or non-fucosylated anti-BAFFR antibody comprises a $V_H$ domain comprising the amino acid sequence of SEQ ID NO: 1 and a $V_L$ domain comprising the amino acid sequence of SEQ ID NO: 2.

12. The lyophilized formulation of claim 1, wherein the hypofucosylated or non-fucosylated anti-BAFFR antibody comprises a heavy chain region comprising the amino acid sequence of SEQ ID NO: 9 and a light chain region comprising the amino acid sequence of SEQ ID NO: 10.

13. A method of treating a disease or disorder that is mediated by BAFF receptor and that can be treated by killing or depleting B cells, comprising administering to a subject, a lyophilized formulation of claim 1.

14. The method of claim 13, wherein said disease or disorder that is mediated by BAFF receptor and that can be treated by killing or depleting B cells is selected from the group consisting of autoimmune disease, B cell neoplasm, lymphoma, leukemia, myeloma, rheumatoid arthritis, systemic lupus erythematosus, multiple sclerosis, and Pemphigus vulgaris.

15. An aqueous pharmaceutical composition having a pH of 6.5 comprising
  (i) a hypofucosylated or non-fucosylated anti-BAFFR antibody wherein the antibody has a concentration of at least 50 mg/ml, and wherein said anti-BAFFR antibody comprises heavy chain CDR1, CDR2 and CDR3 comprising the amino acid sequences of SEQ ID NOs: 3, 4 and 5 respectively, and light chain CDR1, CDR2 and CDR3 comprising the amino acid sequences of SEQ ID NOs: 6, 7 and 8,
  (ii) 270 mM sucrose as a stabilizer,
  (iii) 21 mM histidine as a buffering agent,
  (iv) 0.06% polysorbate as a surfactant, and
  (v) 51 mM arginine.

16. The aqueous pharmaceutical composition of claim 15, wherein the hypofucosylated or non-fucosylated anti-BAFFR antibody has a concentration of 150 mg/ml.

\* \* \* \* \*

SEQUENCE LISTING

```
<160> NUMBER OF SEQ ID NOS: 15

<210> SEQ ID NO 1
<211> LENGTH: 124
<212> TYPE: PRT
<213> ORGANISM: Homo sapiens

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30
```

```
Ser Ala Ala Trp Gly Trp Ile Arg Gln Ser Pro Gly Arg Gly Leu Glu
            35                  40                  45

Trp Leu Gly Arg Ile Tyr Tyr Arg Ser Lys Trp Tyr Asn Ser Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
            115                 120

<210> SEQ ID NO 2
<211> LENGTH: 108
<212> TYPE: PRT
<213> ORGANISM: Homo sapiens

<400> SEQUENCE: 2

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Phe Ile Ser Ser Ser
                 20                  25                  30

Tyr Leu Ser Trp Tyr Gln Gln Lys Pro Gly Gln Ala Pro Arg Leu Leu
            35                  40                  45

Ile Tyr Gly Ser Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Leu Tyr Ser Ser Pro
                 85                  90                  95

Met Thr Phe Gly Gln Gly Thr Lys Val Glu Ile Lys
            100                 105

<210> SEQ ID NO 3
<211> LENGTH: 12
<212> TYPE: PRT
<213> ORGANISM: Homo sapiens

<400> SEQUENCE: 3

Gly Asp Ser Val Ser Ser Asn Ser Ala Ala Trp Gly
 1               5                  10

<210> SEQ ID NO 4
<211> LENGTH: 18
<212> TYPE: PRT
<213> ORGANISM: Homo sapiens

<400> SEQUENCE: 4

Arg Ile Tyr Tyr Arg Ser Lys Trp Tyr Asn Ser Tyr Ala Val Ser Val
 1               5                  10                  15

Lys Ser

<210> SEQ ID NO 5
<211> LENGTH: 12
<212> TYPE: PRT
<213> ORGANISM: Homo sapiens

<400> SEQUENCE: 5
```

```
Tyr Asp Trp Val Pro Lys Ile Gly Val Phe Asp Ser
1               5                   10
```

<210> SEQ ID NO 6
<211> LENGTH: 12
<212> TYPE: PRT
<213> ORGANISM: Homo sapiens

<400> SEQUENCE: 6

```
Arg Ala Ser Gln Phe Ile Ser Ser Ser Tyr Leu Ser
1               5                   10
```

<210> SEQ ID NO 7
<211> LENGTH: 7
<212> TYPE: PRT
<213> ORGANISM: Homo sapiens

<400> SEQUENCE: 7

```
Gly Ser Ser Ser Arg Ala Thr
1               5
```

<210> SEQ ID NO 8
<211> LENGTH: 9
<212> TYPE: PRT
<213> ORGANISM: Homo sapiens

<400> SEQUENCE: 8

```
Gln Gln Leu Tyr Ser Ser Pro Met Thr
1               5
```

<210> SEQ ID NO 9
<211> LENGTH: 454
<212> TYPE: PRT
<213> ORGANISM: Homo sapiens

<400> SEQUENCE: 9

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Gly Trp Ile Arg Gln Ser Pro Gly Arg Gly Leu Glu
            35                  40                  45

Trp Leu Gly Arg Ile Tyr Tyr Arg Ser Lys Trp Tyr Asn Ser Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 10
<211> LENGTH: 215
<212> TYPE: PRT
<213> ORGANISM: Homo sapiens

<400> SEQUENCE: 10

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr Val Ala

```
                 100                 105                 110
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11
<211> LENGTH: 372
<212> TYPE: DNA
<213> ORGANISM: Homo sapiens

<400> SEQUENCE: 11
caggtgcagc tgcagcagag cggcccaggc ctggtcaagc cctctcagac cctgtcactg      60
acctgcgcca tttcaggcga cagcgtgagc agcaacagcg ccgcctgggg ctggatcagg    120
cagagccccg tagggggcct ggaatggctg gcaggatct actacaggtc caagtggtac     180
aacagctacg ccgtgagcgt gaagagcagg atcaccatca ccctgacac cagcaagaac     240 cagttctcac tgcagctcaa cagcgtgacc cccgaggaca ccgccgtgta ctactgcgcc    300
agatacgact gggtgcccaa gatcggcgtg ttcgacagct ggggccaggg caccctggtg    360
accgtgtcaa gc                                                        372

<210> SEQ ID NO 12
<211> LENGTH: 324
<212> TYPE: DNA
<213> ORGANISM: Homo sapiens

<400> SEQUENCE: 12
gatatcgtgc tgacacagag ccccgccacc ctgagcctga gccaggcga gagggccacc      60 ctgtcctgca gggccagcca gtttatcagc agcagctacc tgtcctggta tcagcagaag    120
cccggccagg cccctagact gctgatctac ggcagctcct ctcgggccac cggcgtgccc    180
gccaggttca gcggcagcgg ctccggcacc gacttcaccc tgacaatcag cagcctggag    240
cccgaggact tcgccgtgta ctactgccag cagctgtaca gctcacccat gaccttcggc    300
cagggcacca aggtggagat caag                                            324

<210> SEQ ID NO 13
<211> LENGTH: 184
<212> TYPE: PRT
<213> ORGANISM: Homo sapiens

<400> SEQUENCE: 13

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30
```

```
Val Ala Cys Gly Leu Leu Arg Thr Pro Arg Pro Lys Pro Ala Gly Ala
         35                  40                  45

Ser Ser Pro Ala Pro Arg Thr Ala Leu Gln Pro Gln Glu Ser Val Gly
 50                  55                  60

Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
                 85                  90                  95

Gly Leu Val Ser Trp Arg Arg Gln Arg Arg Leu Arg Gly Ala Ser
                100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
        130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
                180

<210> SEQ ID NO 14
<211> LENGTH: 1419
<212> TYPE: DNA
<213> ORGANISM: Homo sapiens

<400> SEQUENCE: 14
atggcctggg tgtggaccct gcccttcctg atggccgctg cccagtcagt gcaggcccag      60
gtgcagctgc agcagagcgg cccaggcctg gtcaagccct ctcagaccct gtcactgacc     120
tgcgccattt caggcgacag cgtgagcagc aacagcgccg cctggggctg atcaggcag     180 agccccggta ggggcctgga atggctgggc aggatctact acaggtccaa gtggtacaac     240
agctacgccg tgagcgtgaa gagcaggatc accatcaacc tgacaccag caagaaccag      300 ttctcactgc agctcaacag cgtgaccccc gaggacaccg ccgtgtacta ctgcgccaga     360
tacgactggg tgcccaagat cggcgtgttc gacagctggg gccagggcac cctggtgacc     420
gtgtcaagcg ccagcaccaa gggccccagc gtgttccccc tggccccag cagcaagagc       480 accagcggcg gcacagccgc cctgggctgc ctggtgaagg actacttccc cgagcccgtg     540
accgtgtcct ggaacagcgg agccctgacc tccggcgtgc acaccttccc cgccgtgctg     600
cagagcagcg gcctgtacag cctgtccagc gtggtgacag tgcccagcag cagcctgggc     660
acccagacct acatctgcaa cgtgaaccac aagcccagca acaccaaggt ggacaagaga     720
gtggagccca gagctgcgga caagacccac acctgccccc cctgcccagc cccagagctg     780
ctgggcggac cctccgtgtt cctgttcccc ccaagcccca ggacaccct gatgatcagc      840 aggacccccg aggtgacctg cgtggtggtg acgtgagcc acgaggaccc agaggtgaag     900
ttcaactggt acgtggacgg cgtggaggtg cacaacgcca agaccaagcc cagagaggag     960
cagtacaaca gcacctacag ggtggtgtcc gtgctgaccg tgctgcacca ggactggctg    1020
aacggcaagg aatacaagtg caaggtctcc aacaaggccc tgccagcccc catcgaaaag    1080
accatcagca aggccaaggg ccagccacgg gagcccagg tgtacaccct gcccccctcc     1140
cgggaggaga tgaccaagaa ccaggtgtcc ctgacctgtc tggtgaaggg cttctacccc    1200
agcgacatcg ccgtggagtg ggagagcaac ggccagcccg agaacaacta caagaccacc    1260
```

```
cccccagtgc tggacagcga cggcagcttc ttcctgtaca gcaagctgac cgtggacaag    1320
tccaggtggc agcagggcaa cgtgttcagc tgcagcgtga tgcacgaggc cctgcacaac    1380
cactacaccc agaagagcct gagcctgtcc cccggcaag                           1419

<210> SEQ ID NO 15
<211> LENGTH: 705
<212> TYPE: DNA
<213> ORGANISM: Homo sapiens

<400> SEQUENCE: 15
atgagcgtgc tgacccaggt gctggctctg ctgctgctgt ggctgaccgg caccagatgc      60
gatatcgtgc tgacacagag ccccgccacc ctgagcctga gcccaggcga gagggccacc     120
ctgtcctgca gggccagcca gtttatcagc agcagctacc tgtcctggta tcagcagaag     180
cccggccagg ccccctagact gctgatctac ggcagctcct ctcgggccac cggcgtgccc     240
gccaggttca gcggcagcgg ctccggcacc gacttcaccc tgacaatcag cagcctggag     300
cccgaggact tcgccgtgta ctactgccag cagctgtaca gctcacccat gaccttcggc     360
cagggcacca aggtggagat caagcgtacg gtggccgctc ccagcgtgtt catcttcccc     420
cccagcgacg agcagctgaa gagcggcacc gccagcgtgg tgtgcctgct gaacaacttc     480 taccccggg aggccaaggt gcagtggaag gtggacaacg ccctgcagag cggcaacagc     540
caggagagcg tcaccgagca ggacagcaag gactccacct acagcctgag cagcaccctg     600
accctgagca aggccgacta cgagaagcat aaggtgtacg cctgcgaggt gacccaccag     660
ggcctgtcca gccccgtgac caagagcttc aacaggggcg agtgc                     705
```